United States Patent [19]

DeAlberti et al.

[11] 4,414,412

[45] Nov. 8, 1983

[54] PROCESS FOR THE PREPARATION OF UNSATURATED CARBOXYLIC ACIDS BY THE CATALYTIC OXIDATION IN GASEOUS PHASE OF THE CORRESPONDING ALDEHYDES AND CATALYST USED IN SAID PROCESS

[75] Inventors: Giordano DeAlberti, Besnate; Romano Covini; Mario Padovan, both of Milan; Giancarlo Battiston, Baranzate; Guido Petrini, Milan, all of Italy

[73] Assignee: Montedison S.p.A., Milan, Italy

[21] Appl. No.: 629,985

[22] Filed: Nov. 7, 1975

[30] Foreign Application Priority Data

Nov. 12, 1974 [IT] Italy ................ 29321 A/74

[51] Int. Cl.³ .................. C07C 51/26; B01J 23/22; B01J 23/28; B01J 23/30
[52] U.S. Cl. .................. 562/535; 502/317; 502/303
[58] Field of Search .................. 260/530 N; 562/535; 252/462, 467

[56] References Cited

U.S. PATENT DOCUMENTS 3,775,474 11/1973 O'Hara et al. .................. 260/530 N
3,956,377 5/1976 Dolhyj et al. .................. 252/467 X
4,042,533 8/1977 Shaw et al. .................. 260/530

FOREIGN PATENT DOCUMENTS 2448804 4/1975 Fed. Rep. of Germany ... 260/530 N
2456100 6/1975 Fed. Rep. of Germany ... 260/530 N Primary Examiner—W. J. Shine Attorney, Agent, or Firm—Stevens, Davis, Miller & Mosher

[57] ABSTRACT

A process is disclosed for the preparation of acrylic acid or methacrylic acid by reacting in vapor phase acrolein or methacrolein with molecular oxygen or with an oxygen-containing gas, at a temperature between 200° and 350° C., in the presence of a solid catalyst and with a contact time between 0.5 and 5 seconds, characterized in that said catalyst consists of molybdenum, vanadium, tungsten, one or more of the elements selected from the class consisting of silver, titanium, chromium, cerium, lanthanum and tantalum, and oyxgen chemically combined with the above-indicated elements, and wherein the atomic ratios between the various elements present in the catalyst are represented by the empirical formula:

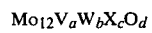

$$Mo_{12}V_aW_bX_cO_d$$

wherein

X represents one or more of the elements Ag, Ti, Cr, Ce, La, Ta;
a varies between 0.5 and 10;
b varies between 0.5 and 8;
c varies between 0.1 and 3 for X=Ag and from 0.3 to 4 for each of the elements Ti, Cr, Ce, La, Ta; with the further proviso that if X consists of 2 or more elements, then their sum shall not exceed 8 atoms; and
d is a number that satisfies the valency requirements of the other elements.

The catalyst may be carried on a support, and the reaction may be carried out in the presence of an inert gaseous diluent or water vapor.

8 Claims, No Drawings

PROCESS FOR THE PREPARATION OF UNSATURATED CARBOXYLIC ACIDS BY THE CATALYTIC OXIDATION IN GASEOUS PHASE OF THE CORRESPONDING ALDEHYDES AND CATALYST USED IN SAID PROCESS

The present invention relates to a process for the preparation of unsaturated carboxylic acids by the catalytic oxidation in vapor phase, with molecular oxygen or an oxygen-containing gas, of unsaturated aldehydes of low molecular weight, containing more than two carbon atoms. This invention is particularly convenient for the production of acrylic acid from acrolein, as well as methacrylic acid from methacrolein.

The process according to this invention is characterized in that the unsaturated aldehyde is oxidized in the presence of a catalyst consisting of molybdenum, vanadium, tungsten, and one or more of the elements selected from the class consisting of silver, titanium, chromium, cerium, lanthanum, tantalum, besides oxygen chemically combined with the above-mentioned elements.

The catalyst according to this invention shows a composition that may vary within very wide limits. It contains from 0.5 to 8 atoms of V and from 0.5 to 8 atoms of W per 12 Mo atoms. Moreover, it contains one or more elements selected from the class consisting of Ag, Ti, Cr, Ce, La and Ta in proportions that will vary from 0.1 to 3 atoms per 12 atoms of Mo in the case of Ag, and from 0.3 to 4 atoms per 12 atoms of Mo in the case of the other elements indicated, provided that in the case there be present two or more of the above indicated elements, the total number of atoms shall not exceed 8 per 12 Mo atoms.

Thus, the composition of the catalyst according to this invention may be represented by the empirical formula:

$$Mo_{12}V_aW_bX_cO_d$$

wherein
- X represents one or more of the elements Ag, Ti, Cr, Ce, La and Ta;
- a varies from 0.5 to 10;
- b varies from 0.5 to 8;
- c varies from 0.1 to 3 for X=Ag and from 0.3 to 4 for each of the elements Ti, Cr, Ce, La, Ta; with the further proviso that in case X consists of 2 or more elements, then their sum shall not exceed 8 atoms; and
- d is a number that satisfies the valency requirements of the other elements.

The oxidation of unsaturated aldehydes to the corresponding acids on catalysts consisting of Mo, V, W, O is already known to the prior art. However, we have found that the addition to the Mo, V, W, O system of the prior art of one or more elements selected from the class consisting of Ag, Ti, Cr, Ce, La and Ta improves in an unpredictable way the catalytic performance. The importance of such an improvement appears clearly from a comparison between the results of Examples 1 to 11 and the results of Examples 12 to 14 as given below.

The catalyst of the present invention may be employed either without a support or with a suitable support such as, for instance, silica, alumina, silica-alumina, silicon carbide, pumice, etc.

Different processes already well known to the prior art may be used for the preparation of the catalyst. More particularly, one may combine in an aqueous medium the compounds comprising the various elements and then subject the resulting suspension to evaporation—if desired after the addition of the aforesaid suitable support to the suspension.

The combination of the various elements composing the catalyst, however obtained, is subjected to calcination in an air stream at a temperature of from 330° to 470° C., for a time not less than two hours.

The process according to this invention may be carried out in any type of conventional reactor suitable for conducting oxidations in gaseous phase. One may use both fixed bed as well as fluid bed reactors.

The reaction temperature is comprised between 200° and 350° C. The reaction may be conducted either at atmospheric or greater than atmospheric pressure up to 10 atm (absolute).

The contact time, defined as the ratio between the apparent volume of the catalyst and the volume of the gas fed in at reaction conditions in a given time unit, is comprised between 0.5 and 5 seconds.

The concentration of unsaturated aldehyde is preferably between 2.5 and 8% by volume with respect to the feed mixture. The molar ratio between the oxygen and the unsaturated aldehyde is preferably between 0.5 and 6. The oxygen necessary for the oxidation process may be fed in the pure state. However, air is the preferred oxidizing agent.

The oxidation reaction is preferably conducted in the presence of one or more diluents such as for instance nitrogen, carbon dioxide, water vapor, etc. Amongst the possible diluents, water vapor is particularly preferred. The water vapor concentration is preferably between 20% and 50% with respect to the feed mixture.

The following examples are given in order more clearly to illustrate the invention, but without limiting its scope.

The terms "conversion" and "selectivity" respectively express:

Conversion of aldehyde in % equals $$\frac{\text{moles of fed aldehyde} - \text{moles of unreacted aldehyde}}{\text{moles of fed aldehyde}} \times 100$$

Selectivity of conversion to product in % equals $$\frac{\text{gram atoms of carbon in the product}}{\text{gram atoms of carbon in the reacted aldehyde}} \times 100$$

EXAMPLE 1

The catalyst of composition $Mo_{12}V_{4.6}W_{2.4}Ti_{2.2}Cr_{0.6}$ was prepared as follows:

To an aqueous solution, containing 58.8 g of $(NH_4)_2Mo_2O_7$, 2.2 g of $(NH_4)_2Cr_2O_7$ and 17.4 g of $(NH_4)_6H_2W_{12}O_{40} \cdot n\ H_2O$ (ammonium tungstate at 90% of $WO_3$), in 90 ml of distilled water, were admixed 15.6 g of $NH_4VO_3$. This mixture was thereupon brought up to 70° C. and then there were added 65.5 g of an aqueous solution of $TiCl_3$ at 15% by weight. Under strong stirring the mixture was then brought to boiling whereupon it was then evaporated to dryness.

After drying in an oven at 130° C., the residue was calcined at 400° C. for 5 hours in a current of air. It was then ground and the fraction between 60 and 80 mesh (Tyler series) was collected.

7 ml of ctalyst were then placed into a tubular steel reactor of 10 mm diameter, thermally stabilized in a bath of molten salts. Thereupon a gaseous mixture containing 7.5% by volume of acrolein, 57.5% of air, and 35% of steam were passed through the catalyst at a linear velocity corresponding to a contact time of 2 seconds, and at a temperature of 280° C.

The results thus obtained were:

| | |
|---|---|
| Conversion of acrolein | 98.8% |
| Selectivity of conversion to acrylic acid | 91.1% |

EXAMPLES 2-14

Catalysts of the compositions indicated in the table below were prepared by following the procedures described in Example 1 and by using as the Ag, Ce and La salts the corresponding nitrates. The Ta (of Example 10) was employed in the form of an insoluble pentoxide, added in a finely subdivided state.

The acrolein was oxidized in the presence of these catalysts as indicated in Example 1, at the temperature and contact times indicated for each case in the table on the following page.

TABLE

| Example | Composition of catalyst | Reaction temperature °C. | Contact time seconds | Acrolein Conversion % | Selectivity to acrylic acid % |
|---|---|---|---|---|---|
| 2 | $Mo_{12}V_2W_{2.4}Ti_{2.2}Cr_{0.6}$ | 300 | 2 | 97.6 | 91.1 |
| 3 | $Mo_{12}V_2W_{2.4}Ti_4$ | 280 | 1 | 97.9 | 85.5 |
| 4 | $Mo_{12}V_6W_{2.4}Ti_{2.2}$ | 270 | 2 | 99.4 | 87.1 |
| 5 | $Mo_{12}V_{4.6}W_{2.4}Cr_{0.6}$ | 280 | 2 | 100 | 78 |
| 6 | $Mo_{12}V_{4.6}W_{2.4}Cr_{0.6}Ce_{2.2}$ | 300 | 2 | 98 | 84 |
| 7 | $Mo_{12}V_{4.6}W_{2.4}Cr_{0.6}Ag_1$ | 260 | 2 | 97.2 | 86.7 |
| 8 | $Mo_{12}V_{4.6}W_{2.4}Cr_{0.6}Ag_{2.2}$ | 260 | 2 | 93.6 | 89.1 |
| 9 | $Mo_{12}V_{4.6}W_{2.4}Cr_{0.6}La_{2.2}$ | 320 | 2 | 99.6 | 85 |
| 10 | $Mo_{12}V_{4.6}W_{2.4}Cr_{0.6}Ta_{2.2}$ | 280 | 2 | 99.6 | 82.4 |
| 11 | $Mo_{12}V_2W_4Cr_{0.6}Ti_{2.2}$ | 280 | 2 | 100 | 91.9 |
| 12 | $Mo_{12}V_2W_{2.4}$ | 280 | 2 | 99.6 | 76.3 |
| 13 | $Mo_{12}V_{4.6}W_{2.4}$ | 260 | 2 | 97.8 | 80.6 |
| 14 | $Mo_{12}V_6W_{2.4}$ | 280 | 2 | 84.8 | 68.1 |

What is claimed is:

1. A process for the preparation of acrylic or methacrylic acid by reacting in vapor phase acrolein or methacrolein with oxygen or with an oxygen-containing gas at from 200° to 350° C., in the presence of a catalyst represented by the empirical formula:

$$Mo_{12}V_aW_bX_cO_d$$

wherein
X is selected from the group consisting of Ti, Ti+Cr, Ag+Cr, La+Cr, and wherein:
a is from 0.5 to 10;
b is from 0.5 to 8;
c is from 0.1 to 3 for Ag and from 0.3 to 4 in the other cases; and
d satisfies the valency requirements of the other elements.

2. A process according to claim 1, wherein the catalyst is carried on a support.

3. A process according to claim 1, wherein the reaction is carried out in the presence of an inert gaseous diluent or steam.

4. A process for the preparation of acrylic or methacrylic acid by reacting in vapor phase acrolein or methacrolein with oxygen or with an oxygen-containing gas, optionally in the presence of steam, at from 200° to 350° C., in the presence of a catalyst represented by the empirical formula:

$$Mo_{12}V_aW_bX_cO_d$$

wherein a, b, and d have the same meanings as in claim 1; c varies between 0.3 and 4; and X is selected from the group consisting of Ti and Ti+Cr.

5. A catalyst having the empirical formula:

$$Mo_{12}V_aW_bX_cO_d$$

wherein a, b and d have the same meanings as in claim 1; c varies between 0.3 and 4; and X is selected from the group consisting of Ti and Ti+Cr.

6. A catalyst having the empirical formula:

$$Mo_{12}V_aW_bX_cO_d$$

wherein a, b, c and d and X have the same meanings as in claim 1.

7. A catalyst having the empirical formula:

$$Mo_{12}V_aW_bLa_cCr_dO_e.$$

wherein
the number of atoms of each element present is represented by a–e;
wherein
a is a number from 0.5–10
b is a number from 0.5–8
c is a number from 0.3–4
d is a number from 0.3–4
e is a number that has satisfied the valence requirements of the other elements present; and wherein the catalyst does not contain cerium.

8. A catalyst composition consisting essentially of an oxide complex of molybedenum, vanadium, tungsten, lanthanum and chromium.

* * * * *